United States Patent [19]

Petasis et al.

[11] Patent Number: 5,087,790
[45] Date of Patent: Feb. 11, 1992

[54] METHOD FOR OLEFINATION OF CARBONYL COMPOUNDS USING TITANOCENE DERIVATIVES

[75] Inventors: Nicos A. Petasis, Hacienda Heights, Calif.; Eugene I. Bzowej, Thornhill, Canada

[73] Assignee: University of Southern California, Los Angeles, Calif.

[21] Appl. No.: 713,907

[22] Filed: Jun. 12, 1991

[51] Int. Cl.$^5$ .................. C07C 11/02; C07C 15/40; C07C 15/44
[52] U.S. Cl. ............................ 585/638; 585/639; 502/349
[58] Field of Search .............. 502/349; 585/524, 638, 585/639

[56] References Cited

U.S. PATENT DOCUMENTS 5,008,302  4/1991  Hüsler et al. .................. 522/14

OTHER PUBLICATIONS

Tebbe et al., "Olefin Homologation with Titanium Methylene Compounds", J. Am. Chem. Soc. 100, 3611-12 (1978).

Pine et al., "Carbonyl Methylation Using a Ti-Al (Tebbe) Complex", J. Org. Chem. 50, 1212-16 (1985).

Grubbs and Tumas "Polymer Synthesis and Organo-transition Metal Chemistry", Science 243, 907-915 (1989).

Takai et al., "Prepr. of Alkenyl Sulfides and Enamines by Alkylidenation of Carboxylic Acid Derivatives", Tetrahedron Lett., 30 211, 1989.

*Primary Examiner*—Asok Pal
*Assistant Examiner*—P. Achutamurthy
*Attorney, Agent, or Firm*—Nilsson, Robbins Dalgarn, Berliner Carson & Wurst

[57]  ABSTRACT

A method for conversion of a starting compound containing a carbon-oxygen double bond to a corresponding product containing a carbon-carbon bond, in particular for conversion of a carbonyl compound to the corresponding olefinic derivative, in which the carbonyl substrate is reacted with an appropriate titanocene derivative. The method is particularly suitable for the olefination of aldehydes, ketones, esters, lactones, amides and lactams. The olefination procedure using these titanocene derivatives proceeds rapidly and in high yield, and is of a more general applicability than heretofore known methods.

16 Claims, No Drawings

METHOD FOR OLEFINATION OF CARBONYL COMPOUNDS USING TITANOCENE DERIVATIVES

BACKGROUND OF THE INVENTION

The present invention relates to synthetic organic chemistry. In particular, the invention relates to a process for the conversion of a carbon-oxygen bond in a carbonyl compound to a carbon-carbon bond. Such process is of value for the preparation of compounds of interest to the chemical, agrochemical and pharmaceutical industries.

The conversion of a carbonyl group (C=O) to an olefin (C=C) is one of the most important synthetic reactions in current use, with numerous applications in research and industry. While a number of methods are known to perform such transformations, these are often restricted to particular types of C=O groups or in the types of C=C they can produce.

The most widely used method for the olefination of aldehydes and ketones is the Wittig reaction and its various modifications, including the Horner-Emmons procedure [J. I. G. Cadogan (ed.), "Organophosphorus Reagents in Organic Synthesis," Academic Press, London (1979); H. J. Bestman et al., Top. Cur. Chem. 109:65 (1983)]. While this is a very general method for the synthesis of olefins, it does not work well for readily enolizable ketones, due to the basic nature of the ylides or phosphonate anions used. Moreover, the Wittig reaction gives different products than the expected olefins with esters, lactones or amides.

Several organometallic reagents involving geminal dimetallic derivatives ($L_nM^1$—CHR—$M^2L_n$) or nucleophilic metallocarbenes ($L_nM$=CHR) are also suitable for the preparation of certain types of olefins or enol ethers. These reagents, however, all have a number of structural limitations and experimental drawbacks. Due to the extreme reactivities of many of the reagents involved, such methods are often unsuitable for routine applications, particularly on a large scale. In addition, the reagents typically require the use of special techniques which may be unsuitable for commercial-scale synthetic procedures.

Known methods for the olefination of esters and lactones include the use of the aluminum-titanium complex known as the Tebbe reagent [F. N. Tebbe et al., J. Am. Chem. Soc. 100:3611 (1078); S. H. Pine et al., J. Am. Chem. Soc. 102:3270 (1980); S. H. Pine et al., J. Org. Chem. 50:1212 (1985)]or the related titanocyclobutanes developed by Grubbs [R. H. Grubbs et al., Science 243:907 (1989)]. Due to difficulties in the preparation of homologated variants, however, both of these methods are limited to methylenations. In addition, the Tebbe reagent is also extremely air-sensitive and must be handled under a highly controlled inert atmosphere with sophisticated equipment. Moreover, this reagent is not reliable in its reactions with various carbonyl compounds, and isolation of products prepared using the reagent involves an elaborate aqueous work-up. A further complication when using Tebbe reagent is the presence of residual reactive aluminum by-products; this can affect yields through side-reactions with some of the products. In this respect, the titanocyclobutane may be advantageous, as it is aluminum free. Unfortunately, the titanacyclobutane currently is prepared from the Tebbe reagent, and thus suffers from some of the same disadvantages. Mechanistically, these reagents are believed to olefinate via the highly reactive carbene complex.

Another titanium-based olefination technique involves the use of the $RCHBr_2$—Zn—$TiCl_4$ system to olefinate a variety of carbonyl compounds, including aldehydes, ketones, esters, lactones, silyl esters and thioesters [K. Takai et al., Tetrahedron Lett. 2417 (1978); K. Takai et al., Tetrahedron Lett. 26:5579,5581 (1985); K. Takai et al., Bull. Chem. Soc. Japan, 53:1698 (1980); T. Okazoe et al., J. Org. Chem. 52:4410 (1987); K. Takai, et al., Tetrahedron Lett. 30:211 (1989)]. While this method can be effective for many substrates, it utilizes somewhat drastic conditions and a more cumbersome experimental procedure. In addition, methylenations of esters or lactones are not always efficient with this method. In any event, the use of homologated variants is limited by the availability of particular $RCHBr_2$ species.

Several other methods have been reported to effect carbonyl olefinations via complexes of zirconium [J. Schwartz et al., Pure App. Chem. 60:65 (1988); J. M. Tour et al., Tetrahedron Lett. 30:3927 (1989)], tantalum [Schrock, R. R., Acc. Chem. Res. 12:98 (1979)] and aluminum [A. M. Piotrowski et al., J. Org. Chem. 53:2829 (1988)]. All of these methods are apparently of a narrow applicability and are limited only to certain substitution patterns. Moreover, these reaction schemes use very costly or highly toxic reagents.

Accordingly, there is a need in the art for a general, practical and convenient method for the conversion of a carbon-oxygen bond to a carbon-carbon bond via olefination of a variety of carbony compounds, particularly esters, lactones, amides and lactams.

It is an object of the present invention to provide a practical and effective method for the conversion of a carbon-oxygen bond to a carbon-carbon bond via conversion of a carbonyl compound to the corresponding olefin, which method obviates the disadvantages attendant to the methods of the prior art.

BRIEF DESCRIPTION OF THE INVENTION

In accordance with the present invention, there is provided a method for conversion of a carbon-oxygen bond to a carbon-carbon bond via conversion of a carbonyl compound selected from the group consisting of aldehydes, ketones, esters, lactones, amides and lactams to the corresponding olefinic derivative (e.g., olefins, enol ether, enamine etc.). This process comprises reacting the carbonyl substrate with an appropriate titanocene derivative. These compounds are readily available and reasonably stable. Due to the simple experimental procedures and product isolation techniques, this method is applicable for the convenient synthesis of a variety of substances.

DETAILED DESCRIPTION OF THE INVENTION

This invention involves the use of particular titanocene derivatives as reagents for the olefination of a wide variety of different carbonyl compounds. Suitable titanocene derivatives have the general formula

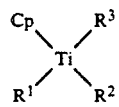

wherein Cp is cyclopentadienyl or substituted cyclopentadienyl; $R^1$ is Cp or $R^4$; and $R^2$, $R^3$ and $R^4$ are independently selected from the group consisting of alkyl, aryl, alkenyl and alkynyl, with the proviso that at least one of $R^2$, $R^3$ and $R^4$ is —$CHR^5R^6$ in which $R^5$ and $R^6$ are non-interfering substituents. In particular, $R^5$ and $R^6$ are independently selected from the group consisting of hydrogen, alkyl, alkenyl, alkynyl, aryl, —$SiR_3$, —$SnR_3$, —SR, —OR and —NRR', wherein each R or R' is independently selected from the group consisting of alkyl and aryl.

A preferred class of these derivatives have the formula 4, wherein R' is selected from the group consisting of hydrogen, aryl, alkyl, alkenyl, alkynyl, —$SiR_3$, —$SnR_3$, —SR, —OR and —NRR, in which each R is independently selected from the group consisting of alkyl and aryl. Reaction of the titanocene derivatives (such as those of formula 4) with carbonyl compounds of formula 5, wherein R" is selected from the group consisting of alkyl, alkenyl and aryl and R''' is selected from the group consisting of hydrogen, alkyl, alkenyl, aryl, —OR and —NRR, in which each R is alkyl or aryl, results in the formation of the corresponding olefinic products of formula 6, wherein R', R" and RR''' are as previously defined. The titanocene derivatives 4 may readily be prepared by the addition of organolithium (M=Li) or organomagnesium (M=MgBr) reagents of formula 3 to titanocene dichloride of formula 2. Compounds 2 and 3 are either commercially available or may be readily prepared in large quantities in a known manner.

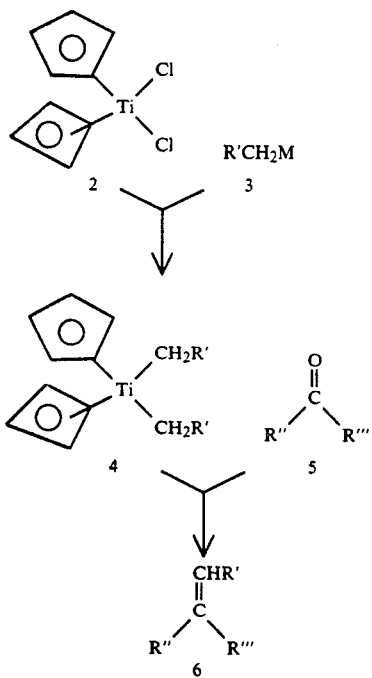

The olefination process is conveniently effected with 1-4 equivalents of the titanocene derivative 4 in solution; suitable solvents include toluene, tetrahydrofuran, hexane, benzene, dichloromethane and dibutyl ether. The reaction may be carried out over a range of temperatures; a particularly suitable temperature range is between about 45 and about 85° C.

In addition to the compounds of formula 4, the titanium reagents $CpTiR^1R^2 R^3$, wherein $R^1$ is other than Cp, similarly should react with a wide range of carbonyl compounds. Due to the fact that these compounds are typically less stable than those of formula 4, they may be utilized at lower temperatures. This allows the olefination of thermally sensitive substrates. These compounds may be prepared by the consecutive addition of $R^1M$, $R^2M$ and $R^3M$ to compounds of the type $CpTiX_3$, in which M=Li or MgBr and X=Cl or other leaving group.

In the foregoing description, the term alkyl refers to unsubstituted or substituted straight-chain or branched groups comprising at least one carbon atom, preferably one to about 10 carbon atoms. The terms alkenyl and alkynyl refer to mono- or polyunsaturated moieties containing at least one carbon-carbon double bond or triple bond, respectively and comprising at least three carbon atoms (i.e., a vinyl group in the case of alkenyl), preferably three to about 10 carbon atoms. The term aryl refers to mono- and polycyclic aromatic groups consisting of carbon and hydrogen (including but not limited to phenyl, naphthyl, anthracyl, etc.), as well as aromatic heterocyclic groups. The term substituted refers to the presence of one or more functionalities which does not interfere (i.e., is a "non-interfering substituent") with the course of the reaction in which a given compound is involved (e.g., formation of the titanocene reagent or olefination). Whether a particular functionality might lead to the formation of complex products through unwanted side-reactions may be determined through routine experimentation. Suitable functionalities which in general do not interfere with the formation of the titanocene reagent include, but are not limited to, alkyl, aryl, alkoxy, ketal and acetal. Similarly, functionalities which in general do not interfere with the olefination reaction include, but are not limited to, alkyl, aryl, alkoxy, trialkylsilyloxy, tertiary amino, ketal, acetal, bromo and chloro.

With reference to the titanocene derivatives of formula 4, a preferred class of compounds for purposes of the invention are those in which R' is hydrogen, alkyl and aryl. Alternative possible embodiments of R' for use in accordance with the present invention include the following: —$SiR_3$ (to give vinyl silanes); —$SnR_3$ (to give vinyl tins); —SR (to give vinyl sulfides); —OR (to give vinyl ethers); —NRR (to give enamines); etc. Accordingly, a very large number of olefinic compounds may be prepared via the method of the present invention.

The preferred titanocene derivatives 4, some of which are known compounds [see. e.g., M. T. Reetz, "Organotitanium Reagents in Organic Synthesis," Springer-Verlag, Berlin (1986); M. Bottrill et al., in "Comprehensive Organometallic Chemistry," Pergamon Press, Oxford, Vol. 3, p. 331 (1982)], are reasonably stable to air and water. As the organotitanium reagents used in the method described herein are much less basic than the reagents employed in the Wittig reaction, moreover, they are effective for the olefination of readily enolizable substrates (unlike, for example, Wittig reagents). The present procedure is also more practical than other titanium-based methods, which may work well for some methylations but not for preparation of other olefins.

The reagents of formula 4 may be suitably prepared in a routine manner from commercially-available precursors and materials which are readily obtainable through a variety of known synthetic routes. For example, dimethyl titanocene (formula 4, R'=H) may be prepared from $Cp_2TiCl_2$ (formula 2) and methyl lithium via a method reported in the literature [K. Claus et al., Ann. Chem. 654:8 (1962)]. The compounds of formula 3 wherein M is lithium are derived, for example, from the corresponding halides or other precursors [see, e.g., B. Wakefield, "Organolithium Methods," Academic Press, London (1988)]. The compounds of formula 3 wherein M is MgBr, commonly known in the art as Grignard reagents, may also be prepared by a number of known methods [see, e.g., J. C. Stowell, "Carbanions in Organic Synthesis," John Wiley & Sons, New York (1979)].

Although some evidence suggests that the thermal decomposition of compounds of formula 4 produces reactive titanocene alkylidenes ($Cp_2Ti=CHR'$), it is believed that in the presence of carbonyl compounds 5 the alkylidenes do not form to any significant extent or are formed while the carbonyl is complexed to the titanium. While the present invention is not bound to any particular theory, it is currently speculated that in the case of dimethyl titanocene, by way of example, carbonyl complexation is followed by methyl group transfer from the titanocene to the carbonyl. Subsequent elimination of methane or Cp would ultimately provide the corresponding olefins. In any event, the mechanism of olefination using compounds of formula 4 is believed to bear little resemblance to the mechanisms of olefination techniques utilizing Tebbe reagent or titanacyclobutanes.

A major advantage of the titanium-based method described herein is that titanium is an abundant, inexpensive and generally nontoxic element. As a consequence, the compounds of general formula 1 show much promise for routine and large scale synthetic applications.

In addition to the dimethyl and dibenzyl titanocenes discussed in the following examples, other titanocene derivatives are capable of this reactivity. For example, similar reactions have been carried out with bis(trimethyl-silylmethyl)titanocene (formula 4; R'=$SiMe_3$), which converts carbonyl compounds to the vinyl silane products.

Mixed derivatives, having two different groups on the titanium, can also be used. In this case reactions involving one of the two groups would predominate, whereby the other group would serve as a "dummy" ligand. Further, a variety of other types of products may be prepared by using more functionalized groups on the titanium in, e.g., the compounds of formula 1.

The process of transforming organometallic precursors to titanocene compounds (for example, the preparation of compounds of formula 4 from those of formula 2) may be more difficult with sterically hindered groups, which may be less readily accommodated on the titanium. Routine experimentation is used to determine appropriate procedures for preparing particular titanocene derivatives.

The reagents generally react readily with the substrates in a desired and predictable fashion. In the case of some bulky titanocene derivatives which may be thermally very stable, elevated temperatures or modified conditions are appropriate. On the other hand, particular titanocene derivatives are highly reactive; therefore, lower temperatures would be suitable. The optimum conditions for each reagent—substrate combination would therefore also be established by experiment, varying such factors as temperature, solvent, etc.

Only one of the two groups (ligands) on the titanium is incorporated into the product. Moreover, particular types of titanocene derivatives are generally less effective in this reaction under the usual conditions. For example, groups having β-hydrogens are known to decompose via β-hydride elimination. These problems may be solved by using an appropriate "dummy" ligand that serves to direct the olefination towards the other ligand and to retard unwanted side-reactions by taking advantage of steric and electronic effects. This is advantageous for less readily available or more expensive ligands, as well as for ligands which might otherwise not be readily utilizable in the olefination reaction. Suitable "dummy" ligands include, but are not limited to, phenyl, pentafluorophenyl and trifluoromethyl.

The product of reaction with the titanocene derivatives in accordance with the present invention is a compound in which a carbon-oxygen double bond of the carbonyl has been replaced by a carbon-carbon double bond. In many instances, the desired final product is the compound containing the carbon-carbon double bond; accordingly, this compound may be isolated from the reaction mixture. In accordance with particular embodiments of the present invention, however, it is contemplated to further react the resultant olefin in situ prior to isolation of the product from the reaction mixture. For example, in some instances it is desired to obtain the corresponding compound containing a carbon-carbon single bond instead of the carbon-carbon double bond. Therefore, in accordance with a particular embodiment of the present invention, it is further contemplated to hydrogenate the crude reaction mixture over Pd/C, or to hydroborate the olefinic product.

The invention may be better understood with reference to the accompanying examples, which are provided for purposes of illustration and should not be construed as in any sense limiting the scope of the invention.

EXAMPLE 1

In a standard procedure, methyllithium (2 equivalents) was added to an ice-cooled suspension of $Cp_2TiCl_2$ in dry ether (15 ml per gram of $Cp_2TiCl_2$). After stirring for one half hour, a small amount of water was added to quench the reaction. The contents were transferred to a separatory funnel and the organic layer washed once with water. Drying with anhydrous $MgSO_4$, filtration, and removal of the solvent with a rotary evaporator provided bright orange crystals of dimethyl titanocene. Yields are typically greater then 95%. Due to its thermal instability and light sensitivity over time in the solid form, this compound is best stored as a 0.5M tetrahydrofuran or toluene solution kept in the dark, and preferably cold. The compound can be exposed to water during the normal workup procedure or to air during weighing and handling. Moreover, the reagent can be stored in the dark as, e.g., a toluene or THF solution for several months without significant decomposition, as indicated by NMR This solution (1-3 equivalents) was then mixed with the carbonyl compound at 50-70° C. for the period of time required for consumption of the starting material (typically in the range of about 3 to several days, depending upon the carbonyl compound). Generally, the more electrophilic the carbonyl group, the less time was required for reaction to occur. The order of decreasing reactivity of carbonyl compounds is generally: aldehydes > ketones > esters and lactones > amides and lactams.

The reaction may be run in a variety of solvents, including benzene, toluene, tetrahydrofuran, dichloromethane, dibutyl ether and hexane. Normally, 1-3 equivalents of a compound of formula 4 (e.q., R'=H) are required for consumption of the starting material. There appears to be a slight rate increase, and thus a more efficient use of the titanocene reagent, on switching from toluene to benzene. This is even more apparent when tetrahydrofuran (THF) replaces benzene; generally, in THF only two equivalents are required for consumption of the carbonyl compound. Work-up of reaction mixtures using these solvents involves precipitation of the by-product (e.g., with petroleum ether/ether), filtration and purification (e.g., by column chromatography). When hexane is used as the solvent, only 1-1.3 equivalents of the compound of formula 4 (e.g., R'=H) are required for complete conversion, although the rate of reaction is somewhat slower (for example, 3-4 days at reflux for esters). The work-up is somewhat easier, as precipitation of the by-product has already occurred and the mixture can be purified directly after filtration (e.g., by placing it directly on a chromatography column). It is believed that the non-polar nature of hexane relative to the other solvents minimizes formation of an unwanted by-product, which may consume one equivalent of the titanocene reagent.

In a typical experiment, a 0.5 M solution of the titanocene in toluene or THF was mixed with the carbonyl compound and stirred under argon in the dark. After allowing the reaction mixture to cool to ambient temperature, it was diluted with petroleum ether or a mix of diethyl ether/petroleum ether (for less soluble products) and precipitation was allowed to occur. Filtration and evaporation of the solvent generally provided a yellow or orange colored product. This product could be purified by column chromatography (for example, flash column chromatography on silica or basic alumina for vinyl ethers) or by distillation when reactions are carried out on a larger scale.

Table I illustrates starting carbonyl compounds, final products and product yields obtained pursuant to the above method. The yields reported (with the exception of entry 7 in Table I) are for reactions run in toluene with 3 equivalents of dimethyltitanocene, typically on a 1 mmol scale; the reaction in entry 7 was carried out with one equivalent of dimethyltitanocene, and the reaction in entry 8 was run with one equivalent of dimethyltitanocene in hexane or with two equivalents of the reagent in THF on a 10-mmol scale. In the cases of entries 4 and 8 in Table I, reactions were also performed in THF with a slightly higher yield in both cases. All products gave satisfactory IR, $^1$H NMR and $^{13}$C NMR data. Yields were not optimized and were determined after chromatographic purification.

Despite increased steric hindrance, the α-substituted aldehyde (entry 2) gave a higher yield than its parent derivative (entry 1), possibly due to slower decomposition of the aldehyde moiety or the resulting olefin. A variety of ketones, including aryl, alicyclic and α,β-unsaturated, were efficiently methylenated. Even readily enolizable ketones, such as entry 5, were smoothly olefinated; this is not the case with Wittig reagents. Esters (entry 8) and lactones (entries 9-11) were similarly converted to the corresponding enol ethers. Selective olefination of a ketone was possible by limiting the amount of reagent (entry 7).

TABLE I

| Entry | Carbonyl compd | Product | Yield % |
|---|---|---|---|
| 1 | CH$_3$(CH$_2$)$_9$-CHO | CH$_3$(CH$_2$)$_9$-CH=CH$_2$ | 43 |
| 2 | CH$_3$(CH$_2$)$_8$-CH(CH$_3$)-CHO | CH$_3$(CH$_2$)$_8$-CH(CH$_3$)-CH=CH$_2$ | 62 |
| 3 | Ph-CO-Ph | Ph-C(=CH$_2$)-Ph | 90 |
| 4 | (cyclic ketone) | (cyclic alkene) | 83 |
| 5 | (2-tetralone) | (methylenetetralin) | 60 |
| 6 | (pinocarvone-type ketone) | (methylenated product) | 61 |

TABLE I-continued

| Entry | Carbonyl compd | Product | Yield % |
|---|---|---|---|
| 7 | cyclopentanone with -(CH2)2-C(O)OCH3 substituent | methylenecyclopentane with -(CH2)2-C(O)OCH3 substituent | 60 |
| 8 | CH3-C(O)-O-(CH2)11CH3 | CH3-C(=CH2?)-O-(CH2)11CH3 (enol ether) | 85 |
| 9 | δ-lactone with Ph substituent | corresponding enol ether | 41 |
| 10 | chroman-2-one (dihydrocoumarin) | 2-methylenechroman | 80 |
| 11 | macrocyclic lactone | corresponding enol ether | 70 |
| 12 | N-phenyl-γ-butyrolactam | N-phenyl-2-methylenepyrrolidine | 55 |

EXAMPLE 2

Dibenzyl titanocene [Cp$_2$Ti(CH$_2$Ph)$_2$] was prepared by a known reaction of titanocene dichloride (Cp$_2$TiCl$_2$) with two equivalents of benzyl magnesium chloride [G. A. Razuvaev et al., Doklady Akad. Nauk. SSR 189:103 (1969); A. Glivicky et al., Can J. Chem. 51:2609 (1973); J. Scholz et al., Chem. Ber. 120:1369 (1987)].

Table II shows the results of benzylidenation with various types of carbonyl compounds. In a typical procedure, a solution of Cp$_2$Ti(CH$_2$Ph)$_2$ (1.45g, 4 mmol, 4 eq.) in toluene (8 ml) was mixed with dodecyl acetate (228 mg, 1 mmol) and heated to 55° C. for 20 hours while stirring under argon in the dark. After cooling, the reaction mixture was diluted with petroleum ether (200 ml) and the resulting yellow-orange precipitate that formed was removed by filtration. Removal of the solvent in vacuo, followed by flash column chromatography (basic alumina, 5% diethyl ether/petroleum ether) yielded the vinyl ether as a colorless oil (212 mg, 70%).

During reactions with carbonyl compounds, Cp$_2$Ti(CH$_2$Ph)$_2$ decomposes faster than Cp$_2$TiMe$_2$. Therefore, the olefination reactions can generally be performed at lower temperature (i.e., about 45-55° C.). For most substrates, the best benzylidenation yields were obtained when 3-4 equivalents of the toluene solution of the titanocene reagent were used.

In general, moderate stereoselectivities in the olefin geometry have been observed in the olefinations reported in Table 2. The more stable isomer predominates, particularly with aromatic carbonyl derivatives. Unless otherwise specified, reactions were run in toluene with 3-4 equivalents of dibenzyl titanocene at 45°-55° C. over 16-26 hours on a 1 mmol scale; yields were determined after chromatographic purification. In the reaction of entry 1, 2 equivalents of 2 were used. The yields in entries 10 and 11 were determined after distillation. All products gave satisfactory IR, $^1$H NMR and $^{13}$C NMR data. The E:Z ratio was tentatively determined by NMR spectroscopy of purified samples.

Although several aldehydes (e.g. entry 1) reacted rather slugglishly with dibenzyl titanocene, the reaction worked well with saturated ketones (entries 2 and 3). With an α,β-unsaturated ketone (entry 4), however, only small amounts of the expected olefin could be obtained in this case, possibly due to a competitive polymerization initiated by conjugate addition of a benzyl radical or other species.

As with dimethyl titanocene, esters (entries 5-8) and lactones (entry 9) reacted smoothly with dibenzyl titanocene to give the corresponding enol ethers. Although these acid sensitive systems can be isolated by chromatography on basic alumina, this process may result in some loss of product. It is also possible to hydrogenate the crude reaction mixture over Pd/C to afford directly the corresponding ethers, or to hydroborate the olefinic product to obtain the corresponding alcohol. While the benzylidenation of formic or acetic esters led predominately to the E-enol ether, this was reversed in the case of aromatic esters and lactones. The Z-isomer was the major product in these substrates, as indicated in ¹H— and ¹³C—NMR chemical shifts and coupling constants.

Finally, amides react to give phenyl-substituted enamines. Since chromatographic purification is often difficult with these products, they are bets isolated by distillation with these products, they are best isolated by predominantly the E-geometry, which would be expected to be more stable for steric reasons.

While the invention has been described with reference to exemplary embodiments thereof, it should be noted by those skilled in the art that the disclosures are exemplary only and that various other alternatives, adaptations and modifications may be made within the scope of the present invention. Accordingly, the present invention is not limited to the specific embodiments as illustrated herein, but only by the following claims.

What is claimed is:

TABLE II

| Entry | Carbonyl compound | Product | Yield % | E:Z ratio |
|---|---|---|---|---|
| 1 | Me(CH₂)₈-CH(Me)-CHO | Me(CH₂)₈-CH(Me)-CH=CH-Ph | 20 | 67:33 |
| 2 | cyclic ketone (spiro) | cyclic =CHPh | 86 | |
| 3 | 2-methylcyclopentanone | 2-methyl-1-(phenylmethylene)cyclopentane | 75 | 50:50 |
| 4 | 4,4-dimethylcyclohex-2-enone | 4,4-dimethyl-1-(phenylmethylene)cyclohex-2-ene | 15 | 48:52 |
| 5 | HCO-OEt | Ph-CH=CH-OEt (H, OEt) | 35 | 74:26 |
| 6 | Me-CO-O(CH₂)₁₁Me | Ph-C(Me)=?-O(CH₂)₁₁Me | 70 | 60:40 |
| 7 | Ph-CO-OMe | Ph-C(Ph)=?-OMe | 84 | 14:86 |
| 8 | 4-Br-C₆H₄-CO-OEt | 4-Br-C₆H₄-C(Ph)=?-OEt | 75 | 15:85 |
| 9 | phthalide C=O | phthalide =CHPh | 70 | 16:84 |
| 10 | H-CO-NMe₂ | Ph-CH=CH-NMe₂ | 48 | >99:1 |
| 11 | Me-CO-NMe₂ | Ph-C(Me)=?-NMe₂ | 45 | 71:29 |

1. A method for conversion of a starting compound containing a carbon-oxygen double bond to a corresponding product containing a carbon-carbon bond, which method comprises:

reacting the compound with a titanocene compound of the formula

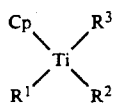

wherein Cp is cyclopentadienyl or substituted cyclopentadienyl;

$R^1$ is Cp or $R^4$; and $R^2$, $R^3$ and $R^4$ are independently selected from the group consisting of alkyl, alkenyl, alkynyl and aryl, with the proviso that at least one of $R^2$, $R^3$ and $R^4$ is —$CHR^5R^6$, in which $R^5$ and $R^6$ are non-interfering substituents, whereby the carbon-oxygen double bond is replaced by a carbon-carbon double bond to provide an olefin.

2. A method according to claim 1, wherein $R^5$ and $R^6$ are independently selected from the group consisting of hydrogen, alkyl, alkenyl, alkynyl, aryl, —$SiR_3$, —$SnR_3$, —SR, —OR and —NRR', wherein each R or R' is independently selected from the group consisting of alkyl and aryl.

3. A method according to claim 1, wherein the starting compound containing a carbon-oxygen double bond is selected from the group consisting of aldehydes, ketones, esters, lactones, amides and lactams.

4. A method according to claim 1, wherein the titanocene compound has the general formula $Cp_2Ti(CH_2R')_2$, wherein R' is selected from the group consisting of hydrogen, aryl, alkyl, alkenyl, alkynyl, —$SiR_3$, —$SnR_3$, —SR, —OR and —NRR, in which each R is independently selected from the group consisting of alkyl and aryl.

5. A method according to claim 4, wherein R' is hydrogen.

6. A method according to claim 4, wherein R' is phenyl.

7. A method according to claim 1, wherein said reacting is carried out in a solution of at least one solvent selected from the group consisting of toluene, tetrahydrofuran, hexane, benzene, dichloromethane and dibutyl ether.

8. A method according to claim 1, wherein at least one equivalent of said titanocene compound is employed.

9. A method according to claim 1, wherein at least two equivalents of said titanocene compound are employed.

10. A method according to claim 1, further comprising recovering the product olefin from the reaction mixture.

11. A method according to claim 10, further comprising reacting the product olefin in situ prior to recovery thereof from the reaction mixture.

12. A method according to claim 11, wherein said reacting comprises catalytic hydrogenation.

13. A method according to claim 11, wherein said reacting comprises hydroboration.

14. A method according to claim 1, wherein said reacting is carried out at a temperature in the range of about 45° C. to about 85° C.

15. A method according to claim 1, wherein the starting compound contains at least two carbon-oxygen double bonds, one of which comprises a ketone or aldehyde function which is selectively olefinated over an ester or amide function.

16. A method according to claim 15, wherein selective olefination is carried out by limiting the amount of reagent to about one equivalent.

* * * * *

UNITED STATES PATENT AND TRADEMARK OFFICE
CERTIFICATE OF CORRECTION

PATENT NO. : 5,087,790
DATED : February 11, 1992
INVENTOR(S) : Petasis et al.

It is certified that error appears in the above-identified patent and that said Letters Patent is hereby corrected as shown below:

Col. 1, line 34 change "$(L_nM^1\text{-}CHR\text{-}M^2L_n)$" to --$(L_nM^1\text{-}CHR\text{-}M^2L_m)$--.

Col. 2, line 33 change "carbony" to --carbonyl--.

Col. 3, line 24 change "RR'''" to --R'''--.

Col. 4, line 51 change "[see." to --[see,--.

Col. 6, line 60 insert --.-- at end of sentence.

Col. 7, line 6 change "(e.q.," to --(e.g.,--.

Col. 11, line 6 change "bets" to --best--.

Col. 11, line 7 delete "with these products, they are best isolated by" and insert -- (entries 10 and 11). These enamines had --

Signed and Sealed this

Eighth Day of June, 1993

Attest:

MICHAEL K. KIRK

*Attesting Officer*   *Acting Commissioner of Patents and Trademarks*